United States Patent
Joelsson et al.

(10) Patent No.: US 11,938,001 B2
(45) Date of Patent: Mar. 26, 2024

(54) MULTIFUNCTIONAL RELEASE LINER FOR DRESSINGS

(71) Applicant: Mölnlycke Health Care AB, Gothenburg (SE)

(72) Inventors: Hans Joelsson, Gothenburg (SE); Linn Liu Hallerstig, Gothenburg (SE); Shiva Eibpoosh, Gothenburg (SE); Annelie Blomqvist, Stenungsund (SE)

(73) Assignee: Mölnlycke Health Care AB, Gothenburg (SE)

( * ) Notice: Subject to any disclaimer, the term of this patent is extended or adjusted under 35 U.S.C. 154(b) by 610 days.

(21) Appl. No.: 17/057,176

(22) PCT Filed: May 28, 2019

(86) PCT No.: PCT/EP2019/063880
§ 371 (c)(1),
(2) Date: Nov. 20, 2020

(87) PCT Pub. No.: WO2019/229090
PCT Pub. Date: Dec. 5, 2019

(65) Prior Publication Data
US 2021/0186765 A1 Jun. 24, 2021

(30) Foreign Application Priority Data
May 30, 2018 (EP) .................................. 18175192

(51) Int. Cl.
*A61F 13/02* (2006.01)
*A61F 13/00* (2006.01)

(52) U.S. Cl.
CPC .............................. *A61F 13/0266* (2013.01); *A61F 2013/00574* (2013.01); *A61F 2013/00812* (2013.01); *A61F 2013/00817* (2013.01)

(58) Field of Classification Search
CPC .......... A61F 13/00008; A61F 13/00021; A61F 13/0246; A61F 13/0253; A61F 13/0266;
(Continued)

(56) References Cited

U.S. PATENT DOCUMENTS

| | | | |
|---|---|---|---|
| 5,985,395 A * | 11/1999 | Comstock | A61B 46/00 206/440 |
| 2004/0049146 A1 * | 3/2004 | Kolte | A61F 13/0203 602/61 |
| 2010/0106120 A1 * | 4/2010 | Holm | A61F 13/105 602/54 |

FOREIGN PATENT DOCUMENTS

| | | | | |
|---|---|---|---|---|
| DK | 160407 B | * | 3/1991 | |
| EP | 2658937 B1 | * | 3/2017 | B41J 11/002 |

(Continued)

OTHER PUBLICATIONS

Machine translation of DK 160407 B (Year: 1991).*
(Continued)

*Primary Examiner* — Caitlin A Carreiro
(74) *Attorney, Agent, or Firm* — Ballard Spahr LLP

(57) ABSTRACT

A dressing is described having a backing layer, an (absorbent) pad, an adhesive coating and a release liner. The release liner is releasably attached to the adhesive coating. The release liner is configured to stiffen up and protect protrusions and/or border portions of the dressing that may otherwise be wrinkled, folded, kinked or otherwise damaged or impaired prior to (transportation or storage) or during application at the point-of-use. The dressing can be used for wound treatment. The dressing can prevent shearing and/or friction from causing (deep tissue) skin damage.

16 Claims, 4 Drawing Sheets

(58) Field of Classification Search
CPC ...... A61F 13/02; A61F 13/00; A61F 13/0259; A61F 13/60; A61F 2013/00574; A61F 2013/00812; A61F 2013/00217; A61F 2013/00089; A61F 2013/00582
USPC ................ 602/41–43, 52, 54, 57–58, 61
See application file for complete search history.

(56) References Cited

FOREIGN PATENT DOCUMENTS

| WO | WO 2017/081012 | 5/2017 |
|----|----------------|--------|
| WO | WO 2017/220401 | 12/2017 |
| WO | WO 2017/220402 | 12/2017 |

OTHER PUBLICATIONS

International Search Report and Written Opinion dated Aug. 20, 2019 by the International Searching Authority for International Application No. PCT/EP2019/063880, filed on May 17, 2019 and published as WO 2019/229090 on Dec. 5, 2019 (Applicant—Mölnlycke Health Care Ab) (8 Pages).

* cited by examiner

MULTIFUNCTIONAL RELEASE LINER FOR DRESSINGS

CROSS-REFERENCE TO RELATED APPLICATIONS

This application is a U.S. National Phase Application of International Application No. PCT/EP2019/063880, filed May 28, 2019, which claims priority to European Application No. 18175192.6, filed May 30, 2018, each of which are hereby incorporated by reference in their entirety.

TECHNICAL FIELD

The present invention relates to a dressing comprising a backing layer, a pad, an adhesive coating and a release liner. Said release liner is releasably attached to an adhesive coating. The release liner is configured to stiffen up and protect protrusions and/or border portions of the dressing, which may otherwise be wrinkled, folded, kinked or in any way damaged or impaired, for example during transportation or storage, or during application at the point-of-use.

The dressing of the present invention is suitable for wound treatment and wound prevention, in particular for wound prevention, further particular for application onto contoured body parts.

BACKGROUND

Dressings of various sizes and shapes that have more sophisticated release liners are know from the art, in principle, for example from WO 2017/081012, WO 2017/220401 or WO 2017/220402 (all assigned to Mölnlycke Health Care). The release liners protect the dressing from contamination prior to use, and may also facilitate application of the dressing, thus increasing functionality and durability of the dressing in use.

WO 2017/220401 and WO 2017/220402 disclose dressings adapted to be applied to contoured body parts, i.e. particularly the sacrum and the heel, respectively. These dressings are suitable for preventing pressure ulcers. These types of dressings may be comparatively large and may have protrusions, i.e. areas that extend beyond the characteristic extensions of the overall dressing, for example border regions at the edges of such dressings Issues of stability that may arise in for such dressings having one or more protrusion is perhaps best exemplified in FIG. 1, which shows two commercially available dressings for application onto contoured body parts, in particular the heel (FIG. 1*a*) and the sacrum (FIG. 1*b*). For example, protrusions (103*a*, 103*a'*) and (103*b*, 104*b'*) of a thinner border region (102, 102') extend beyond the thicker pad (101, 101'), by a distance d1'.

Typically, each dressing is packed into a single pack, and then a number of single packed dressings are packed into a larger packaging, such as a carton box. During storage and transport, the protrusions may fold or wrinkle when pressed against an inner surface of the single pack. Besides impairing the visual appearance of the dressing when removed from the package, such folding or wrinkling may have an effect on the dressing's stay-on ability. There is a risk that wrinkles formed turn into compartments for body fluids, eventually leading to fluid accumulation and reduced stay-on ability. These potential problems may be exacerbated for larger dressings and/or for dressings that have comparatively limited intrinsic stiffness, for example because the dressings have to be thin or comparatively flexible.

Even if such "flexible" dressings or dressings with portions that are susceptible to bending are temporarily protected and supported by a stiff or otherwise particularly designed packaging, dressings must eventually be taken out of the packaging, handled by a patient or caregiver and must ultimately be applied, which again, may cause the dressing to get wrinkled, wrapped, kinked or otherwise impaired during the application process (i.e. before all release liners are removed and the dressing is securely placed on the patient).

Therefore, one object underlying the present application is to provide a dressing that has protrusions, wherein the problems associated with such dressings, as outlined above, are avoided or mitigated.

SUMMARY OF THE INVENTION

These and other problems are at least partially solved by a dressing having a maximum lateral (X2) (i.e. "sideways") and a maximum longitudinal (Y2) (i.e. perpendicular to the "sideways" extension and preferably along a line of symmetry) extension; wherein said dressing has at least one protrusion, wherein said protrusion has a lateral (X1) or a longitudinal (Y1) extension, or both, that is less than 50% of the maximum lateral (X2) or the maximum longitudinal (Y2) extension, or both, of the overall dressing;
wherein said dressing has a first side and a second opposing side, the first side comprising an adhesive coating having a skin-facing surface adapted to detachably adhere the dressing to a dermal surface, wherein the dressing comprises a release liner that is releasably attached to the adhesive coating;
wherein said release liner has an area of increased thickness or of increased stiffness, or both, in at least part of the area of said at least one protrusion, and in a part of the area outside of said at least one protrusion (but not in the entire area outside of said at least one protrusion);
wherein said increased thickness or increased stiffness, or both, is or are measured vis-à-vis the thickness or stiffness, or both, of the release liner in the remaining area, i.e. the area in which the release liner is not reinforced in regard to thickness and/or stiffness (which is the "remaining area").

In embodiments, the dressing comprises
  a backing layer;
  a pad contoured by a pair of lateral edges, wherein said lateral edges preferably extend essentially in parallel to each other in the longitudinal direction, and contoured by a pair of longitudinal edges, wherein said longitudinal edges preferably extend essentially in parallel to each other in the lateral direction;
  wherein said pad is arranged between said backing layer and said adhesive layer.

In accordance with the present invention, a "protrusion" is a segment of the dressing that extends beyond the central area of the dressing and is characterized by (maximum) lateral and longitudinal extensions that are 50% or less than the respective (maximum) lateral and longitudinal extensions of the overall dressing. An example of a protrusion is segment (103*a*/103*a'*) in FIG. 1*a*/1*b*, segment 203 in FIG. 2 or segment (303) in FIG. 3.

While a part of the outline of the protrusion is defined by and coincides with the outer contour of the overall dressing, the remainder of the protrusion is defined by an imaginary line that separates the remaining area of the dressing from the protrusion. Such a separating line for protrusions (203) and (303) is shown as a dotted line in FIGS. 2 and 3, respectively. The exact position of this (imaginary) line is of no relevance for the present invention as the "reinforced" (increased thickness and/or stiffness) release liner of the present invention extends past this imaginary line and covers not only at least a part of the protrusion, but also at least a part of the remaining area of the dressing. This ensures that the protrusion "benefits" from the stability and stiffness of the overall dressing, in particular of the remaining area.

In embodiments of the present invention, the release liner has an area of increased thickness and/or increased stiffness in the entire area of the protrusion, and in a part of the area outside of said at least one protrusion.

In embodiments of the present invention, said area of said at least one protrusion is from 100 mm² to 5000 mm², preferably from 100 mm² to 2000 mm², wherein said remaining area is from 500 mm² to 50000 mm², preferably from 1000 mm² to 40000 mm².

In embodiments of the invention, the dressing comprises a pad, preferably an absorbent pad and the backing layer extends beyond the periphery of said pad to define a border portion along at least a part of the contour of said pad, preferably along the entire contour of said pad.

The presence and relevance of such a border portion is perhaps best illustrated in FIGS. 1a and 1b, which show dressings (100, 100') having a border portion (102, 102') running around the entire periphery of the pad (101, 101') but being particularly pronounced—and defining protrusions (103a, 103a') and (103b, 103b')—in the bottom part of the dressings.

This border portion of a dressing is generally significantly more flexible and less rigid than the inside (central) part of the dressing ("remaining area") that is reinforced by a pad.

Therefore, this border portion, or parts thereof, may generally be more susceptible to wrinkling, folding, kinking etc.

Therefore in embodiments of the invention, at least parts of the border portion are encompassed by the area of the release liner that is of increased thickness or of increased stiffness, or both.

In embodiments of the present invention, at least a part of the border portion defines at least a part of a protrusion. In preferred embodiments at least a part of the border portion is a protrusion.

In embodiments of the present invention, the dressing comprises a central segment and a border portion, wherein the thickness of the central segment is from 1 mm to 20 mm, preferably from 2 mm to 10 mm, while the thickness of the border portion is from 10 μm to 200 μm, preferably from 20 μm to 100 μm.

In embodiments of the invention, the maximum distance d1 between a lateral or a longitudinal (i.e. the outermost) edge of at least one protrusion (in particular a border portion) to the closest edge of said pad, in particular measured from the outer edge of the protrusion (border portion) to the outer edge of said pad is from 10 mm to 80 mm, e.g. from 25 mm to 60 mm.

In embodiments of the present invention, at least two lateral and/or at least two longitudinal edges of the border run essentially in parallel.

In accordance with the present invention, lateral (longitudinal) edges of the border run "essentially in parallel" if a secant or a tangent for a given lateral (longitudinal) edge can be defined that encompasses said lateral (longitudinal) edge, and a second lateral (longitudinal) edge is present, for which also such an "encompassing" secant or tangent can be defined, wherein the angle between these two secants or tangents of these two lateral (longitudinal) edges have an angle with respect to each other that is 0 degrees+/−degrees, preferably 0 degrees+/−20 degrees. For (fully) parallel edges, the two secants tangents have an angle of 0 degrees.

In general, the release liner acts as a barrier that can protect the sterility of dressing including all of its layers before the dressing is used.

As used herein, the term "releasably attached" means that the release layer may be peeled away from the rest of the dressing by hand.

In embodiments of the present invention, removable portions of the release liner are releasably connected to each other, meaning that they are connected such that the portions remain connected absent a separation force applied to one or all of the portions, and where the portions are capable of being separated upon the application of a separation force.

Specifically in the regard to the realization of the release liner as being divided into at least two different portions, the respective content of WO 2017/081012 is relevant and is incorporated by reference.

The realization of the release liner as two or more separate portions that can be removed separately, respectively, preferably divided along dividing lines, is preferred.

A realization of the release liner as one integral unit, having an area of increased thickness or stiffness, or both, is also within the scope of the present invention.

In embodiments of the invention, if two or more separate portions of the release liner are present, these two or more separate portions may be of the same material or may be of different materials.

In accordance with the present invention, the primary function of the adhesive coating is to adhere the release liner to the remainder of the dressing. As will be outlined in more detail below, the adhesive coating may also be realized as an adhesive layer and may also, preferably, function as or be part of a wound (body) contact layer.

In embodiments of the present invention, the adhesive coating is applied directly onto the pad or onto the release liner or onto both.

In embodiments, the adhesive coating is realized as a layer that has a skin-facing surface and a non-skin-facing surface and that preferably has a thickness of from 5 μm to 100 μm, further preferably of from 10 μm to 60 μm.

In embodiments of the present invention, the adhesive coating or layer fully or partly covers the pad.

In embodiments of the present invention, the adhesive coating is configured to also function as a wound contact layer, preferably wherein the adhesive coating is a coating comprising silicone gel.

In accordance with the present invention, the release liner of the dressing has an area of Increased thickness or of increased stiffness, or both, in at least part of the area of said at least one protrusion and in a part of the area outside of said at least one protrusion ("thicker/stiffer area"), but not in the entire area outside of side protrusion.

The increased thickness or increased stiffness, or both, is or are measured vis-à-vis the thickness or stiffness, or both, of the release liner in the remaining area, i.e. the area that is not reinforced in regard to thickness and/or stiffness ("remaining area").

In embodiments of the invention, the increased thickness of the release liner in said at least part of an area of said at least one protrusion and in said part of the area outside of said at least one protrusion is from 100 μm to 500 μm, preferably from 150 μm to 400 μm, further preferably from 180 μm to 300 μm, and wherein the thickness of the release liner in said remaining area is from 20 μm to 200 μm, preferably from 20 μm to 180 μm, further preferably from 50 μm to 150 μm.

In embodiments of the invention, the increased thickness of the release liner in said at least part of an area of said at least one protrusion and in said part of the area outside of said at least one protrusion is greater by at least 25%, preferably by at least 40% than the thickness of the release liner in said remaining area.

In embodiments of the invention, the increased stiffness of the release liner, as defined by the load at material deformation in said at least part of an area of said at least one protrusion and in said part of the area outside of said at least one protrusion is from 25 N to 150 N, preferably from 40 to 80 N, wherein the stiffness of the release liner in said remaining area is from 10 N to 60 N, preferably from 20 to 40 N, as measured according to the method described below.

Without wishing to be bound by theory, it is believed that if the stiffness of the dressing is too low; i.e. below the range given above for the stiffness of the remaining area, there is not sufficient protection against wrinkle formation when packed in a single-pack. On the other hand, if the dressing is "too stiff"; i.e. above the range specified, the dressing may actually damage the single pack by "cutting/sticking through the paper or plastic single pack of the dressing.

In embodiments of the invention, the stiffness of the release liner, defined by the load at material deformation in said area of said at least one protrusion and in said part of said area outside of said at least one protrusion, is greater by at least 25%, preferably by at least 40% than the stiffness of the release liner in said remaining area, wherein said stiffness is measured according to the method described in the specification.

In embodiments of the present invention the "stiffer" part of the release liner may be reinforced vis-à-vis the remaining part of the release liner by way of including one or more additional material layer(s), for example a nonwoven or a plastic film, and/or by way of embossing this part of the release liner, thereby rendering the release liner stiffer.

In principle, no limitations exist in regard to the material used for the release liner, as long as different degrees of thickness and/or stiffness can be adjusted and the liner material is otherwise flexible enough to conform to the contour of a body.

In embodiments of the present invention, the release liner is or comprises polyurethane, polyethylene or polypropylene, or any combination thereof, in particular low density polyurethane.

In embodiments of the present invention, the release liner comprises polyethylene, polyester, polypropylene or silicone coated paper. For example, the release liner may be a polyethylene film having a thickness in the range of from 30 to 300 μm, e.g. from 50 to 150 μm.

In embodiments the thicker and/or stiffer part of the release liner encompasses at least 15%, preferably at least 20%, further preferably at least 25% of the overall area of the release liner, while, at the same time, encompassing less than 75%, preferably less than 50%, further preferably less than 40% of the of the overall area of the release liner.

In embodiments of the present invention, the dressing has only one axis of symmetry or has no axis of symmetry.

In preferred embodiments of the present invention, the dressing has one axis of symmetry, wherein said symmetry axis also encompasses said at least one protrusion, wherein said symmetry axis also encompasses said part of the area outside of said at least one protrusion that is also of said increased thickness or said increased stiffness, or both.

In embodiments of the present invention, said (exactly) one axis of symmetry coincides with the maximum longitudinal extension Y2.

In embodiments of the present invention the dressing is divided into three separate zones along the longitudinal (y) extension of the dressing: one central zone and two lateral zones, wherein the release liner is of increased thickness and/or stiffness in the central zone.

In embodiments of the present invention, the dressing is configured for use so that the portion of the release liner that is of increased thickness and/or increased stiffness is removed first. This embodiment preferably applies to a dressing that is primarily intended to be used for the sacrum.

In other embodiments, the sequence can also be reversed, i.e. the portion of the release liner that is not of increased thickness and/or increased stiffness is removed first. This embodiment may apply to a dressing that is primarily intended to be used for the heel.

In exemplary embodiments, instructions and/or visual indicators may be associated with the release liner(s) to facilitate the removal of the release liner as well as application of the dressing onto the skin of a human body.

In embodiments of the present invention, the dressing comprises at least one gripping tab; preferably wherein the gripping tab is coplanar with and projecting outwardly from the periphery of the dressing. For example, the gripping tab projects outwardly from the border portion of the dressing.

In embodiments of the present invention, said dressing is a dressing for application to a contoured body part, in particular the sacrum, heel, elbow, knee and the like.

In embodiments of the present invention the dressing as described herein is used in prevention and/or in treatment or wound care, preferably in prevention.

DETAILED DESCRIPTION

The present invention will now be described more fully hereinafter with reference to the accompanying drawings, in which currently preferred embodiments of the present invention are shown. The present invention may, however, be embodied in many different forms and should not be construed as limited to the embodiments set forth herein; rather, these embodiments are provided for thoroughness and completeness, and to more fully convey the scope of the present invention to the skilled person.

The adhesive used in the adhesive coating is preferably skin-friendly and sufficiently adherent to skin such that the dressing stays in place, and maintains its adherence with repeated removal and re-application. The adhesive should be easy to remove without causing trauma.

In embodiments of the invention the adhesive comprises a silicone gel, preferably a soft silicone gel. Examples of suitable silicone gels include the two component RTV systems, such as Q72218 (Dow Corning), and SilGel 612 (Wacker Chemie AG), as well as NuSil silicone elastomers.

In embodiments of the present invention, the adhesive layer of the dressing covers at least 50% of the surface of the pad, preferably at least 60%, further preferably at least 70% of the pad. This ensures or at least facilitates the overall dressing to sufficiently adhere to the skin of a patient during use.

The adhesive layer may be perforated or non-perforated.

In embodiments of the present invention, the adhesive layer may be configured to be a body contact layer As used herein, the term "body contact layer" means the layer that is in contact with the skin of a wearer.

In the field of medical dressings, in particular, wound dressings, a film provided with an adhesive layer for adhering to the patient is often referred to as a wound contact layer. The dressing of the invention may be used on a human body area which has no wound, and therefore the combined film and adhesive layer will be referred to as a body contact layer.

The film onto which the adhesive layer is applied in such a body/wound contact layer may be comprised of a thin plastic film, or a laminate comprising a thin plastic film. Suitable materials for the film include, but are not limited to breathable polyolefin based films (such as polyethylene), polyamide, polyester polyurethane, and silicone. A suitable material for use as the film is a thin polyurethane film. For example, the film of the body contact layer may be a polyurethane film having a thickness of from 15 and 100 µm, e.g. from 40 to 80 µm, preferably from 45 to 60 µm.

Figure 1A:
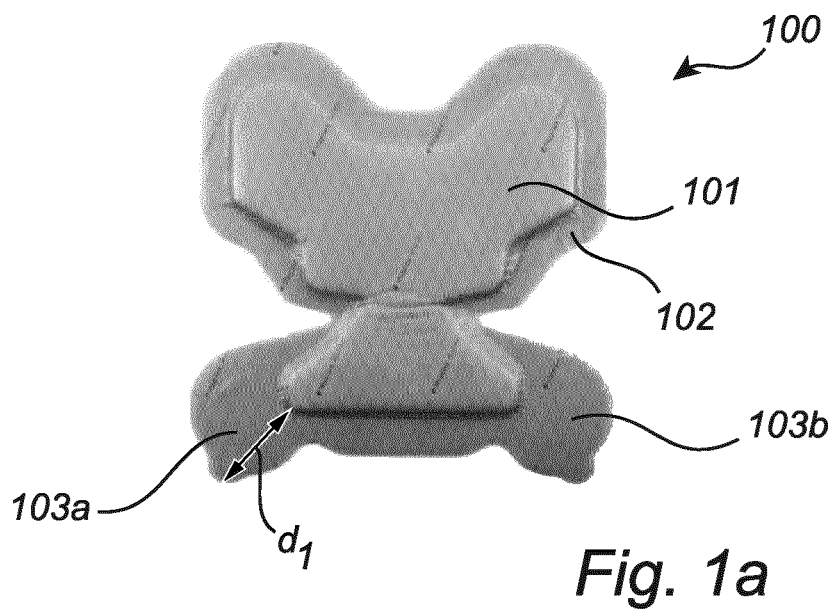
FIG. 1 shows two commercially available dressings for application on a contoured body part, in particular the heel (FIG. 1a) and the sacrum (FIG. 1b).
Figure 1B:
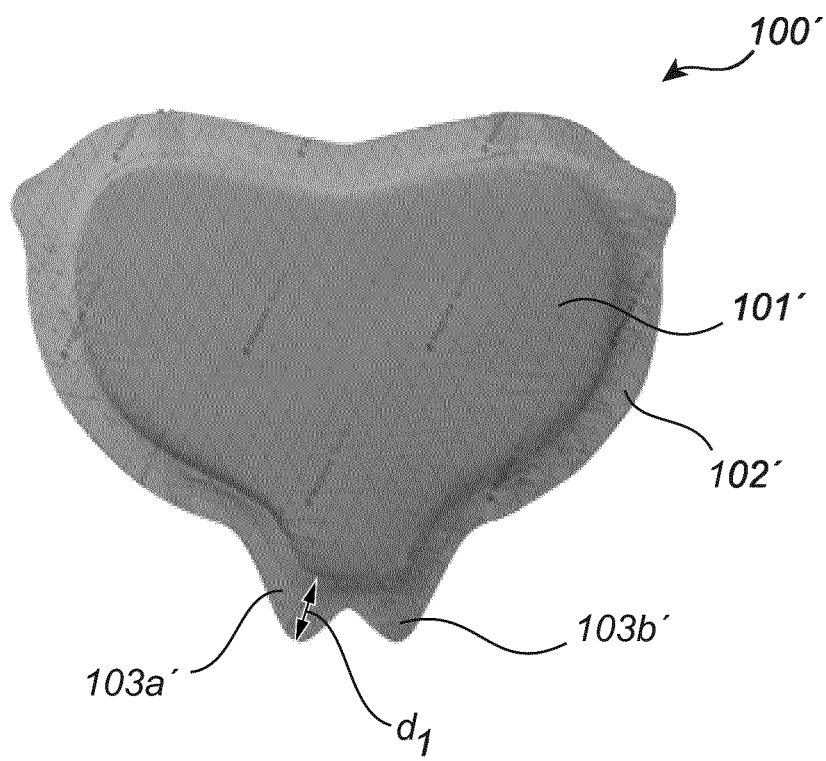
Figure 3:
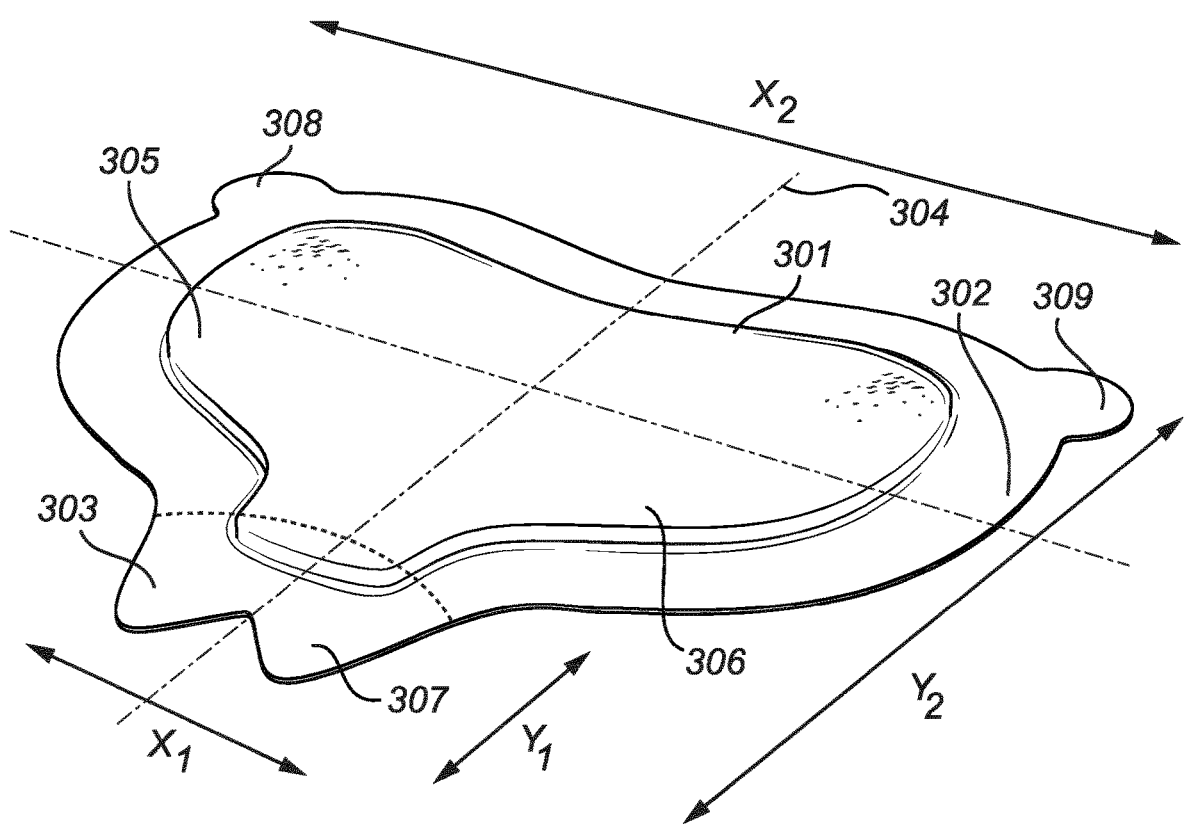
FIG. 3 shows a dressing suitable for the sacrum that has one axis of symmetry and a "w"-shaped protrusion at the bottom end.

As already discussed above, in embodiments of the present invention, the dressing comprises a border portion [see, e.g. (102 and 102') in FIG. 1a/1b or (302) in FIG. 3]. In embodiments, at least the backing layer extends beyond the periphery of the (absorbent) pad to define a border portion around the contour of the pad, or also only parts of the pad. In FIG. 1, the backing layer and the adhesive layer extend beyond the periphery of the pad to define a border portion around the contour of the pad.

The adhesive layer is preferably co-extensive with the backing layer, and has the same outer dimensions (lateral and longitudinal extension, including all protrusions).

In embodiments of the invention, and in particular in order to achieve sufficient adhesion properties, the border portion has a width of 5 to 60 mm and extends along at least parts of the contour of the pad, preferably along the entire pad.

A smaller sized dressing may have a smaller border portion than a larger sized dressing.

In embodiments of the invention, the dressing as such and hence if present, the corresponding border portion, may be substantially heart shaped such that a first and a second lobed portion form part of the lobed upper sides of a heart shape (see FIG. 3). The dressing has an axis of symmetry (304), a maximum lateral extension X2 and a maximum longitudinal extension Y2.

In this illustrative embodiment, the dressing is symmetric about a longitudinal center line (304) and comprises a first lobed portion (305) one side of the longitudinal center line (304), and a second lobed portion (306) on the other side of the longitudinal center line. The first and second lobed portions (305 and 306) are separated by a forked portion ("w"-portion) (307) which replaces the pointed lower part of a heart shape. The forked portion (307) as such is a protrusion or may be seen as comprising a protrusion on either side of an interstice located coaxially with the longitudinal center line. Either way, this protrusion or these two protrusions are advantageously protected from wrinkling or kinking by incorporating a reinforced (increased thickness or stiffness or both) part of the release liner, in accordance with the present invention.

As used herein, the term "lobed portion" means a curved or rounded portion of the dressing. In embodiments, the tab projects "outwardly" from the border portion. In this connection it should be understood that inwardly means a direction towards the inner perimeter of the border area, i.e. a direction towards the pad, while outwardly is an opposite direction.

The dressing has a border region (302) and a pad (301), as well as gripping tabs (308) and (309). The shape of this preferred dressing is adapted to fit to the sacral region of a human body. The forked portion allows for improved stay-on ability in the gluteal cleft region. It is important that this kind of dressing remains adhered in this region since otherwise body fluids (for example as a result of incontinence) may enter into the dressing and impair the adhesion to the skin.

The maximum extension of the protrusion in the lateral (x) direction, X1, is from 10% to 40% of the maximum extension X2, of the overall dressing in the lateral (x) direction.

The maximum extension X2 of such a preferred sacrum dressing is typically in the range of from 12 to 30 cm, preferably from 15 to 20 cm. The maximum extension X1 of the protrusion is preferably in the range of from 2 to 10 cm, e.g. from 4 to 7 cm, depending on the size of the dressing.

In embodiments of the present invention, the pad is arranged to taper downwards, towards the lower region and has a more narrow width in the lower region of the dressing. This shape of the pad allows for proper protection of the coccyx, which is a bony prominence at risk for the development of pressure ulcers. Such a pad also conforms well to the body in the gluteal cleft region. As illustrated in FIG. 3, this part of the pad (301) may also be part of the protrusion (303) and therefore also aid in increasing the stability/stiffness of said protrusion, preferably together with a reinforced release liner. In embodiments of the present invention, the pad is absorbent. The pad may be comprised of one layer or of a plurality of layers.

In embodiments of the present invention, the backing layer of the overall dressing is a thin film, sheet or membrane that is vapor permeable and waterproof. Examples of suitable materials for the backing layer include, but are not limited to polyurethane, polyethylene or polyamide films, silicone films, polyester based nonwoven materials, and laminates of polyester-based nonwoven materials and polyurethane films.

In embodiments of the invention, the backing layer is a polyurethane film and preferably has a thickness of from 5 to 40 µm, e.g. from 15 to 25 µm.

The backing layer may be partly or fully bonded to the pad, for example, via an adhesive such as a pressure sensitive adhesive (e.g. an acrylic adhesive).

In embodiments, the dressing comprises at least one gripping tab; the gripping tab preferably being coplanar with and projecting outwardly from the periphery of the dressing [see (308) and (309) in FIG. 3].

The gripping tab guides the caregiver to lift the dressing, inspect the skin underneath the dressing, and to thereafter re-apply the dressing onto the skin (in case the skin looks ok). Inspection of skin may still be required, albeit on a less frequent basis when the dressing is transparent.

In embodiments, the gripping tab is made in one piece with and projecting outwardly from the border. The gripping tab may be made of the same materials as the border portion, e.g. it may be made from the backing layer and the body contact layer. Hence, the border portion may extend uninterrupted from the border to the gripping tab. This may be beneficial from a manufacturing perspective. However, in at least some exemplary embodiments the gripping tab may be made from a different (or same) material and attached to the border portion.

Since the inspection of the skin typically takes place where the patient is lying on the side in the bed, in preferred embodiments that apply for a sacrum dressing in particular, the dressing comprises at least two gripping tabs such that the caregiver can lift the dressing regardless of which side the patient lies. Hence, in embodiments, the gripping tab is a first gripping tab, and the dressing further comprises a second gripping tab that is coplanar with and projects outwardly from the second lobed portion.

Figure 4:
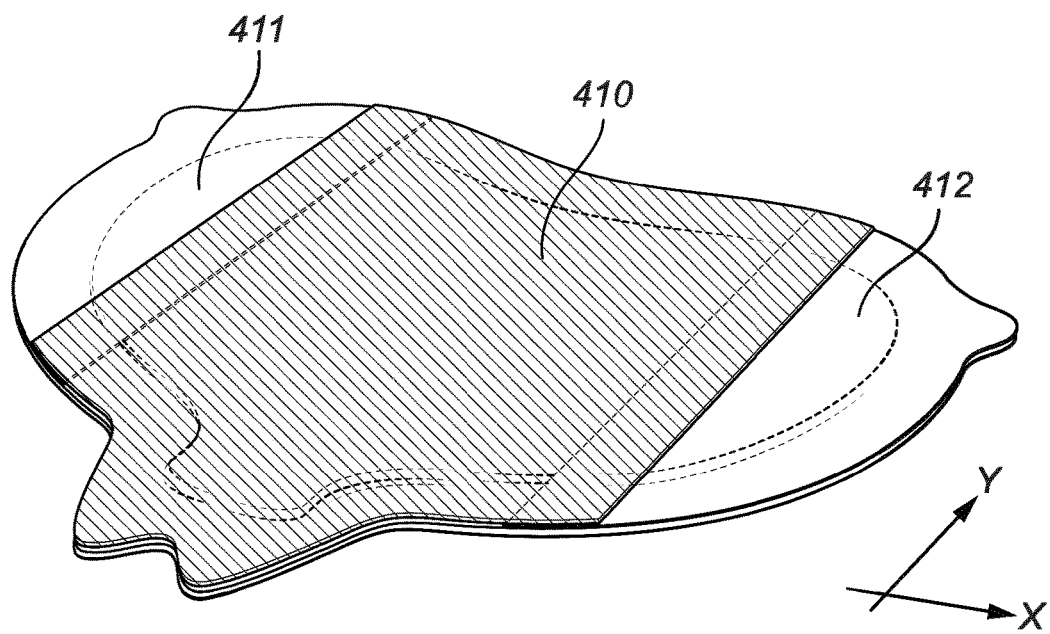
FIG. 4 shows an embodiment in accordance with the present invention: the central area of a three-part release liner is of increased thickness and/or of increased stiffness and covers and stiffens up the bottom protrusion.

As best illustrated in FIG. 4, the dressing may be divided into three separate zones along the longitudinal (y) extension of the dressing: one central zone (410) and two lateral zones (411 and 412), preferably wherein the central part of the release liner is the reinforced part of the release liner, i.e. is of increased thickness or stiffness, or both (see hatched area). As mentioned hereinbefore, the release liner covering the central zone (410) of the dressing is preferably removed first. The release liners (411 and 412) are preferably thinner and/or less stiff than the central part. In order to facilitate smooth application of the dressing onto the skin of a patient.

Figure 2:
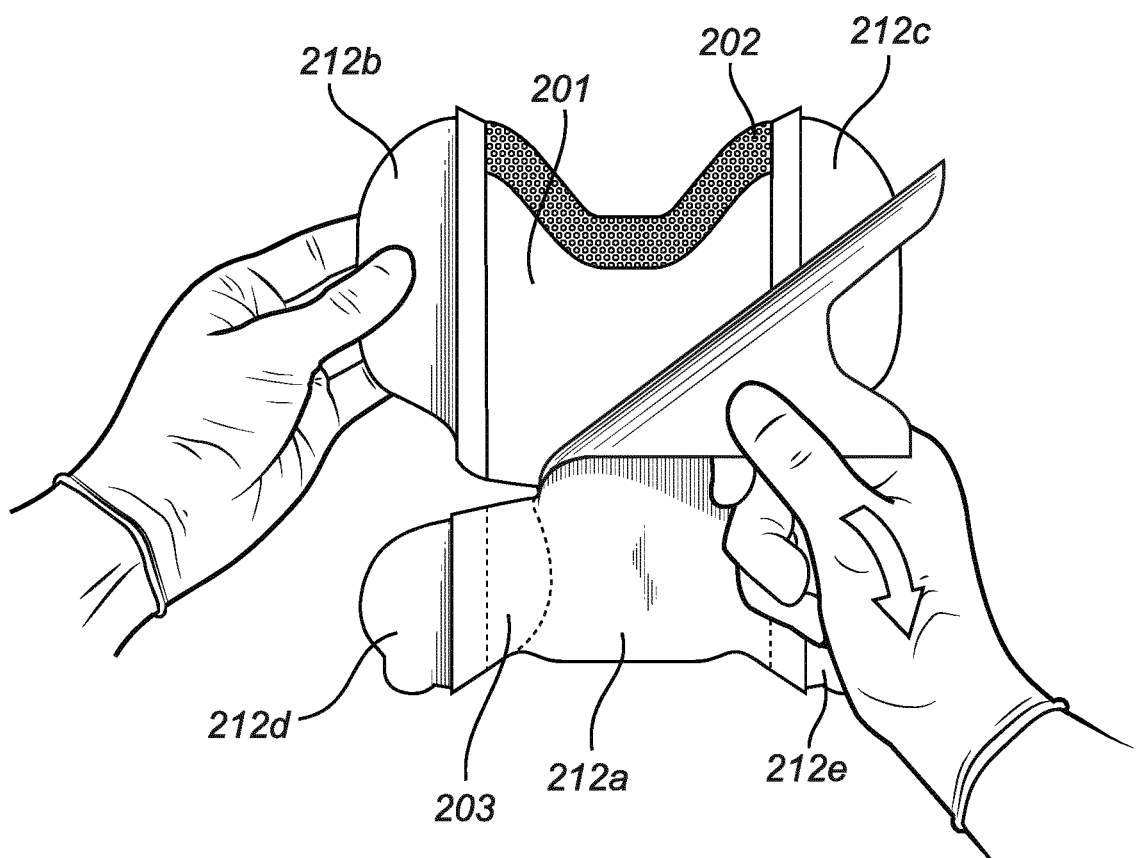
FIG. 2 illustrates the dressing of FIG. 1a, wherein the central release liner is peeled off.

Referring back to FIG. 2, illustrating a heel dressing, the central release liner (212*a*) is preferably removed first. Subsequently, the remaining release liner portions (212*b*-212*e*) are removed and the dressing is gently applied to the body of a patient. In the embodiment illustrated in FIG. 2, the central part of the release liner (212*a*) may be the stiff and/or thick release liner portion (as long as it provides sufficient coverage and protection of the protrusions). Alternatively, the release liner portions 212*b*-212*e* are stiffer and/or thicker than the central portion (212*a*).

Figure 5:
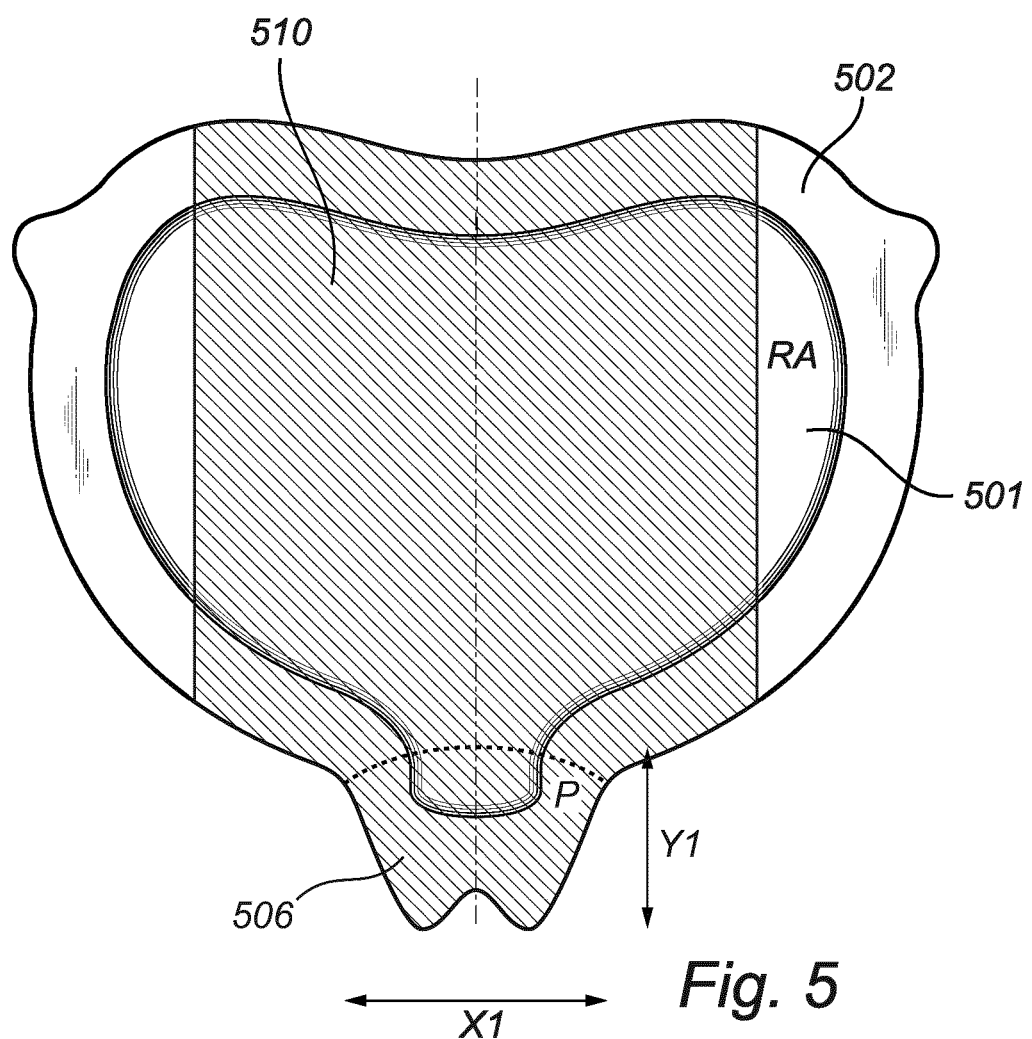
FIG. 5 shows a dressing according to one exemplary embodiment of the invention.

The characteristic dimensions of an exemplary dressing are further exemplified in FIG. 5, showing the bottom view of a sacrum dressing having a pad (501) and a border portion (502). Protrusion (P) comprising the "w"-shaped extension (506) is separated by an (imaginary) dotted line from the remaining area (RA). As can be seen from this exemplary embodiment, the protrusion comprises the "w"-shaped part of the border portion, but also the narrow part of the pad. In this embodiment, the reinforced release liner (509, hatched area) not only covers the entire protrusion, but also a significant part of the remaining area, thus stabilizing the protrusion.

Measurement of the Release Liner Stiffness (Standard: ASTM D882-12)

Test specimens for a release liner having a width of 25 mm and a length of 150 mm were punched out from two different polyethylene films: one having a thickness of 100 μm and a basis weight of 92 g/m² (sample A) and one having a thickness of 200 μm and a basis weight of 184 g/m² (sample B). A tensile tester (Insight MTS) was used to determine the elastic modulus and the peak load at deformation of the materials. The tensile tester was calibrated according to the apparatus (tensile tester: Insight, supplier MTS, year 2008) instructions and set to zero. The samples were mounted in the clamps and the test speed was set to 50 mm/min. The gauge length was 80 mm.

The tensile tester was started and the samples were elongated until break or until reaching 100% elongation. Measurements resulting from premature failures (i.e. the sample breaking at the clamp, or becoming damaged during preparation) were ignored.

The tensile force and elongation were measured during the entire test, and the following results were obtained from the measurements:

Peak load (N)—the maximal load recorded during the test
Strain at peak load (%)
Young's modulus at 10% strain was obtained by the following formula:
$E_{10\%}$=Stress at 10% strain/0.1 (the calculations were based on data points before deformation of the material had begun; i.e. before data plot becomes linear)

The results are summarized in table 1 below.

| Sample | Peak load at deformation (N) | Young's Modulus at 10% strain (kPa) |
| --- | --- | --- |
| Sample A | 23.0 | 85.1 |
| Sample B | 50.2 | 93.8 |

The invention claimed is:

1. A dressing having a maximum lateral (X2) and a maximum longitudinal (Y2) extension;
    wherein said dressing has at least one protrusion, wherein said at least one protrusion has a lateral (X1) or a longitudinal (Y1) extension, or both, that is less than 50% of the maximum lateral (X2) or the maximum longitudinal (Y2) extension, or both, of the dressing;
    wherein said dressing has a first side and a second opposing side, the first side comprising an adhesive coating having a skin-facing surface adapted to detachably adhere the dressing to a dermal surface,
    wherein the dressing comprises a release liner comprising a first portion and a second portion configured to be removed separately, wherein said first portion and said second portion are releasably attached to the adhesive coating;
    wherein said first portion of said release liner covers at least a part of an area of said at least one protrusion, and a part of an area outside of said at least one protrusion,
    wherein a thickness or stiffness, or both, of said first portion of the release liner is higher than a thickness or stiffness, or both, of said second portion of said release liner,
    wherein said thickness or stiffness, or both, of said first portion and said second portion, respectively, are measured in an unfolded area thereof.

2. The dressing according to claim 1, wherein said dressing further comprises
    a backing layer;
    a pad contoured by a pair of lateral edges, wherein said lateral edges extend essentially in parallel to each other in the longitudinal direction, and contoured by a pair of longitudinal edges, wherein said longitudinal edges extend essentially in parallel to each other in the lateral direction;
    wherein said pad is arranged between said backing layer and said adhesive layer.

3. The dressing according to claim 2, wherein said backing layer extends beyond the periphery of said pad to define a border portion along at least a part of a contour of said pad.

4. The dressing according to claim 3, wherein at least a part of the border portion defines at least a part of a protrusion.

5. The dressing according to claim 3, wherein a maximum distance d1 between a lateral or a longitudinal edge of at least one protrusion to a closest edge of said pad, in particular from the outer edge of said protrusion to the outer edge of said pad is from 10 mm to 80 mm.

6. The dressing according to claim 1, wherein the dressing has only one axis of symmetry or has no axis of symmetry.

7. The dressing according to claim 6, wherein the dressing has one axis of symmetry, wherein said symmetry axis also encompasses said at least one protrusion, wherein said symmetry axis also encompasses said part of the area outside of said at least one protrusion that is also of said higher thickness or stiffness, or both.

8. The dressing according to claim 1, wherein the thickness of the release liner in the first portion is in the range of from 50 μm to 1000 μm, and wherein the thickness of the release liner in the second portion is lower than in the first portion, and is in the range of from 10 μm to 500 μm.

9. The dressing according to claim 1, wherein the release liner has an increased thickness in the first portion relative to the second portion, wherein the increased thickness of the release liner in the first portion is greater by at least 25% than the thickness of the release liner in the second portion.

10. The dressing according to claim 1, wherein the release liner has an increased stiffness in the first portion relative to the second portion, wherein the increased stiffness of the release liner in the first portion, as defined by a load at material deformation in said area of said at least one protrusion and in said part of the area outside of said at least one protrusion is from 25 N to 150 N, wherein the stiffness of the release liner in said second portion is from 10 N to 60 N, as measured according to ASTM D882-12.

11. The dressing according to claim 1, wherein the release liner has an increased stiffness in the first portion relative to the second portion, wherein the stiffness of the release liner, defined by a load at material deformation in said area of said at least one protrusion and in said part of said area outside of said at least one protrusion, is greater by at least 25% than the stiffness of the release liner in said second portion, wherein said stiffness is measured according to ASTM D882-12.

12. The dressing according to claim 1, wherein at least one protrusion has a lateral (X1) extension or a longitudinal (Y1) extension of 30% or less of the maximum lateral (X2) or of the maximum longitudinal (Y2) extension, or of both, of the overall dressing.

13. The dressing according to claim 1, wherein said dressing is a dressing for application to a contoured body part, in particular the sacrum, heel, elbow, knee and the like.

14. The dressing according to claim 1, wherein the dressing comprises at least one gripping tab.

15. A method comprising a step of applying the dressing of claim 1 to a wound, thereby treating the wound.

16. The dressing according to claim 1, wherein the release liner further comprises a third portion being releasably attached to the adhesive coating,
   wherein the third portion is separate from the first portion and the second portion,
   wherein the thickness or stiffness, or both, of the release liner is increased in the first portion relative to a thickness or stiffness, or both, of the third portion,
   wherein said thickness or stiffness, or both, of said first portion and said second portion, respectively, are measured in an unfolded area thereof,
   wherein the first portion is a central portion arranged between the second portion and the third portion along an axis of the dressing.

* * * * *